United States Patent
Richert et al.

(10) Patent No.: US 11,933,748 B2
(45) Date of Patent: Mar. 19, 2024

(54) METHOD OF DETERMINING THE THREE-DIMENSIONAL STRUCTURE OF MOLECULES IN CRYSTALLINE INCLUSION COMPLEXES

(71) Applicants: Clemens Richert, Stuttgart (DE); Felix Krupp, Stuttgart (DE); Wolfgang Frey, Stuttgart (DE)

(72) Inventors: Clemens Richert, Stuttgart (DE); Felix Krupp, Stuttgart (DE); Wolfgang Frey, Stuttgart (DE)

(73) Assignee: BRUKER AXS GmbH, Karlsruhe (DE)

( * ) Notice: Subject to any disclaimer, the term of this patent is extended or adjusted under 35 U.S.C. 154(b) by 0 days.

(21) Appl. No.: 17/767,068

(22) PCT Filed: Oct. 6, 2020

(86) PCT No.: PCT/EP2020/078004
§ 371 (c)(1),
(2) Date: Apr. 7, 2022

(87) PCT Pub. No.: WO2021/069444
PCT Pub. Date: Apr. 15, 2021

(65) Prior Publication Data
US 2022/0373482 A1  Nov. 24, 2022

(30) Foreign Application Priority Data
Oct. 10, 2019 (DE) .................... 10 2019 007 099.2

(51) Int. Cl.
G01N 23/207 (2018.01)
C30B 7/06 (2006.01)
(Continued)

(52) U.S. Cl.
CPC ............. *G01N 23/207* (2013.01); *C30B 7/06* (2013.01); *C30B 29/54* (2013.01); *G16C 20/20* (2019.02); *G01N 2223/604* (2013.01)

(58) Field of Classification Search
CPC .. G01N 23/207; G01N 2223/604; C30B 7/06; C30B 29/54; G16C 20/20; G16C 20/00
See application file for complete search history.

(56) References Cited

FOREIGN PATENT DOCUMENTS

WO WO 2016/139373    9/2016
WO WO-2016139373 A1 * 9/2016

OTHER PUBLICATIONS

Schwenger et al. "Tetrakis(dimethoxyphenyl)adamantane (TDA) and its Inclusion Complexes in the Crystalline State: A versatile Carrier for Small Molecules", Wiley-VCH Verlag GmbH & Co. KGaA, Weinheim, Chem. Eur. J. 2015, p. 8781-8789. (Year: 2015).*

(Continued)

*Primary Examiner* — David P Porta
*Assistant Examiner* — Mamadou Faye
(74) *Attorney, Agent, or Firm* — Jaquelin K. Spong

(57) ABSTRACT

The invention is directed to a method for elucidating the three-dimensional structure of compounds by X-ray diffraction (X-ray SCD) characterized in that the compound is co-analyte crystallized with tetraaryladamantanes according to general formula I Wherein R and R' are identical or different residues selected from the group consisting of O—R1, S—R1, NHR1, NR1R2, F, Cl, Br or I and R1, R2 stand for identical or different, substituted on not substituted aliphatic or aromatic residues having 1 to 25 carbon atoms and the the three-dimensional structure of the compound is obtained by X-ray diffraction (X-ray SCD).

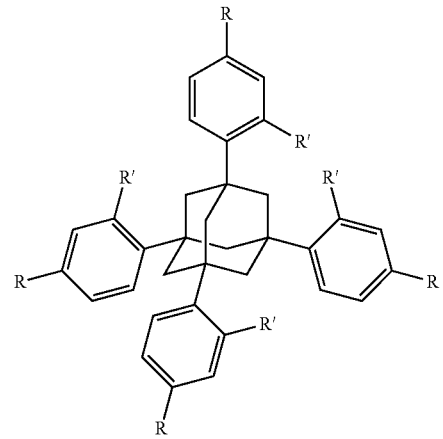

8 Claims, 5 Drawing Sheets

Figure 1:
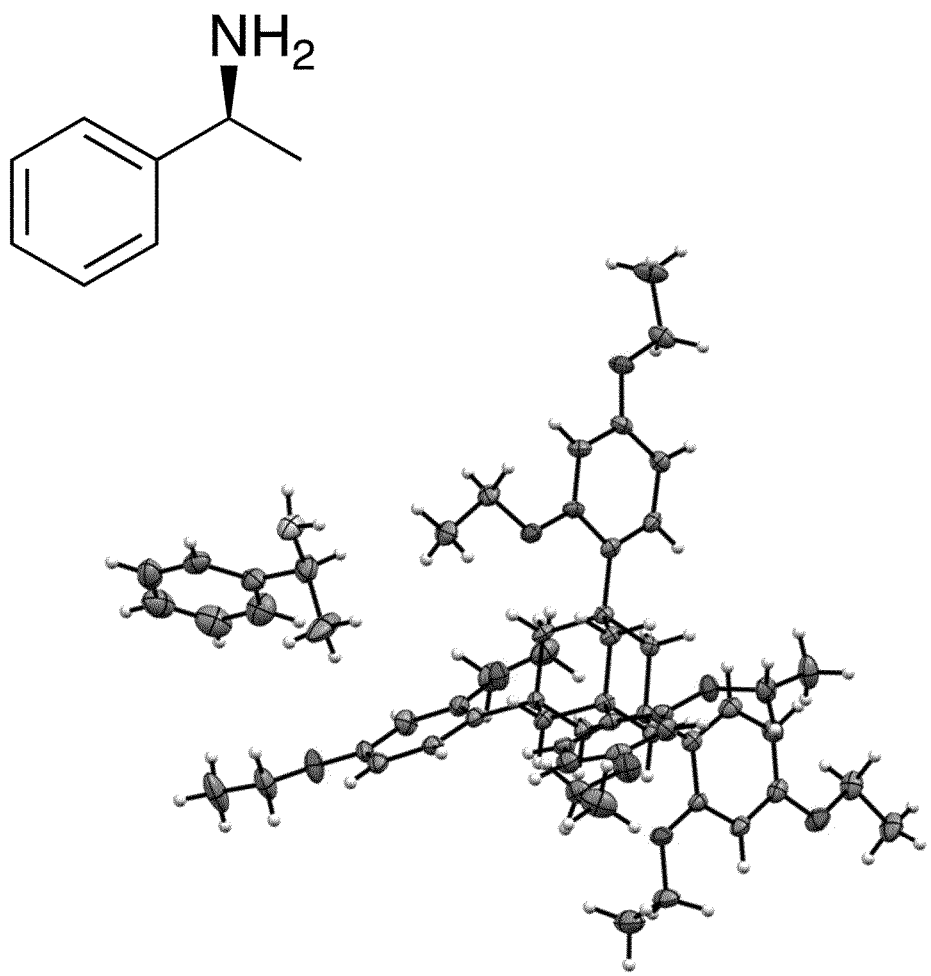

(51) Int. Cl.
*C30B 29/54* (2006.01)
*G16C 20/20* (2019.01)

(56) References Cited

OTHER PUBLICATIONS

Houssein et al. "Porous Materials Based on 3-Dimensional Td-Directing Functionalized Adamantane Scaffolds and Applied as Recyclable Catalysts", ACS Publications 2018, Chem. Mater, Dec. 26, 2018, p. 619-642 (Year: 2018).*

* cited by examiner

TEO / (S)-(-)-1-phenylethylamine 1:1, triclinic, $R_1 = 0.038$, $\chi = 0.14$ TEO / (R)-(+)-1-phenylethylamine 1:1, triclinic, $R_1 = 0.034$, $\chi = 0.02$ TEO / nicotine 2:1, triclinic, $R_1 = 0.048$, $\chi = 0.0$ TEO / (−)-α-thujone 1:1, triclinic, $R_1 = 0.049$, $\chi = -0.07$ TBro / farnesol 4:1,
triclinic, $R_1 = 0.074$ TBro / citronellal 4:1,
triclinic, $R_1 = 0.048$

METHOD OF DETERMINING THE THREE-DIMENSIONAL STRUCTURE OF MOLECULES IN CRYSTALLINE INCLUSION COMPLEXES

The invention is directed to using crystalline inclusion complexes of tetraaryladamantanes (TAAs) to determine the three-dimensional structure of guest molecules.

TECHNICAL FIELD

The determination of the three-dimensional structure of molecules is important. Molecules of different stereochemical configuration have different activity in biological systems and other chiral environments, making it imperative to know what the three-dimensional structure of compounds is that are to be used as active pharmaceutical ingredients, agrochemicals, diagnostic compounds, reagents, or any other use that exposes these molecules to such environments. One example of a chiral compound that is an active pharmaceutical ingredient is thalidomide. The (R)-(+)-enantiomer and the (S)-(−)-enantiomer of thalidomide have different biological activity, including the extent of protein binding in the body and the extent to which they cause birth defects.

Developing new analytical methods for the elucidation of three-dimensional structure of molecules is very important. The most common analytical method that provides direct insights into the three-dimensional structure of molecules, including the absolute configuration, is single-crystal X-ray diffraction (X-ray SCD). Another method providing information on chirality is circular dichroism, but there is no well-established protocol for obtaining the absolute configuration of chiral molecules from CD spectra. Recently, experiments with electron beams were reported to lead to the elucidation of three-dimensional structures (Pantelic et al, Angew. Chem. Int. Ed. 2018, 57, 16313), but this technique is not accessible to typical analytical laboratories.

The use of X-ray crystallography for the elucidation of the three-dimensional structure requires single crystals. Obtaining single-crystals of sufficient quality for X-ray diffractometry is difficult. Many molecules do not crystallize, and even successful crystallizations can be difficult to reproduce. Screening crystallization conditions is time consuming and requires larger quantities of compounds. Small molecules and acyclic molecules that lack ring structures do not tend to crystallize.

Crystalline inclusion complexes consisting of host molecules that provide a framework for crystallization and guest molecules that are included in the crystalline framework are known. Examples include Dianin's compound (A. P. Dianin, J. Russ. Phys. Chem. Soc. 1914, 46, 1310), organic cages (C. J. Pedersen, J. Am. Chem. Soc. 1967, 89, 2495), and crystalline molecular sponges (Y. Inokuma, S. Yoshioka, J. Ariyoshi, T. Arai, Y. Hitora, K. Takada, S. Matsunaga, K. Rissanen, M. Fujita, Nature 2013, 495, 461).

Molecular sponges have been used for elucidating the three-dimensional structure of molecules, but the method has severe limitations. It is limited to molecules that diffuse into the crystalline lattice and then bind to specific positions of the lattice in ordered fashion. Many molecules do not fulfil these criteria. Further, the protocol for structure elucidation is slow (Fujita et al. IUCrJ 2016, 3, 139). The published protocol requires 16 days for each soaking experiment, including 14 days of crystal growth/solvent exchange and 2 days for the soaking itself (Y. Inokuma, S. Yoshioka, J. Ariyoshi, T. Arai, M. Fujita, Nature Protocols 2014, 9, 246). Screening for other solvents is often required. Once suitable crystals are generated, structure elucidation with conventional X-ray-based methods can be very difficult, time consuming and is often unsuccessful because the signals obtained for the guest molecules are much weaker than those for the host (T. R. Ramadhar, S.-L. Zheng, Y.-S. Chen, J. Clardy, Acta Cryst A 2015, 71, 46). Synchrotron radiation, to obtain more signal, is not accessible to most scientists. Molecules without functional groups that engage in specific interactions with the metal-organic framework of the sponges cannot be studied successfully.

Accordingly, object of the Invention was to provide a method for elucidating the three-dimensional structure of molecules which do not crystallize in a manner suitable for single-crystal X-ray diffraction (X-ray SCD) or crystallize too slowly.

It was found that tetraaryladamantanes (TAAs) crystallize without the help of covalent bonds or strong directional interactions, such as hydrogen bonds and are able to encapsulate a wide range of molecules in their crystal lattices.

Upon crystallization, tetraaryladamantanes include a wide range of different guest molecules in their crystals (A. Schwenger, W. Frey, C. Richert, Chem. Eur. J. 2015, 21, 8781). Among the TAAs that show this property are 1,3,5,7-tetrakis(2,4-dimethoxyphenyl)adamantane (TDA),1,3,5,7-tetrakis(2,4-diethoxyphenyl)adamantane (TEO) (P.-E. Alexandre, A. Schwenger, W. Frey, C. Richert, Chem. Eur. J., 2017, 23, 9018), and 1,3,5,7-tetrakis(2-bromo-4-methoxyphenyl)adamantane (TBrO) (F. Krupp, W. Frey, C. Richert, Angew. Chem. Int. Ed. 2020, 59, 15875). The crystallization process is fast (within minutes or hours) and most often leads to inclusion of one molar equivalent of guest molecules or more. The term "Encapsulating Organic Crystals" (EnOCs) has been proposed for such TAAs (C. Richert, F. Krupp, Synlett 2017, 28, 1763). Encapsulation has been proposed to be useful for the capture and release of molecules (A. Schwenger, W. Frey, C. Richert, Angew. Chem. Int. Ed. 2016, 55, 13706), but not for structure elucidation.

Object of the invention is therefore a method for elucidating the three-dimensional structure of compounds by X-ray diffraction (X-ray SCD) characterized in that the compound is co-crystallized with tetraaryladamantes according to general formula I

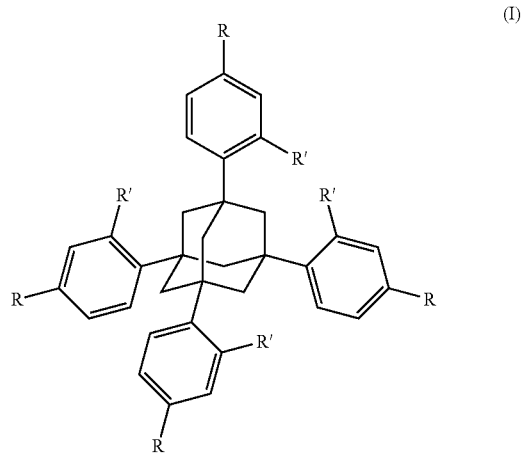

(I)

Wherein R and R' are identical or different residues selected from the group consisting of O—R1, S—R1, NHR1, NR1 R2, F, Cl, Br or I and R1, R2 stand for identical or different, substituted on not substituted aliphatic or aromatic residues having 1 to 25 carbon atoms,
and the the three-dimensional structure of the compound is obtained by X-ray diffraction (X-ray SCD).

Co-crystallization of the molecule whose three-dimensional structure is to be determined (analyte) and one or several tetraaryladamantes to give encapsulating organic crystals (C. Richert, F. Krupp, *Synlett* 2017, 28, 1763) was found to give crystals suitable for the elucidation of the three-dimensional structure of the analyte by X-ray based structure elucidation.

Preferable, 1,3,5,7-tetrakis(2,4-dimethoxyphenyl)adamantane (TDA),1,3,5,7-tetrakis(2,4-diethoxyphenyl)adamantane (TEO) (P.-E. Alexandre, A. Schwenger, W. Frey, C. Richert, *Chem. Eur. J.,* 2017, 23, 9018), or 1,3,5,7-tetrakis(2-bromo-4-methoxyphenyl)adamantane (TBrO) (F. Krupp, W. Frey, C. Richert, Angew. Chem. Int. Ed. 2020, 59, 15875) are used as tetraaryladamantes.

The co-crystallization is performed as known in the art, for example by dissolving the compound to be analysed and tetraaryladamantes in an appropriate solvent and slowly evaporating the solvent to form a single-crystal. The ratio between the compound to be analysed and tetraaryladamantes can be easily determined whether or not single crystals are formed and is usually in a 1:10 to 10:1 molar ratio.

The compounds to be analysed are not particular limited. Of course, the method is valuable for compounds which do not crystallize at all, or which crystallize in a manner not suitable for single-crystal X-ray diffraction (X-ray SCD), or do not crystallize in a reproducible manner. Preferable the method of the invention is used to obtain the absolute or relative stereochemical configuration of chiral molecules as compounds to be analysed.

The compound to be co-crystallized may be a pure enantiomer, but also a mixture of enantiomers like a racemate. The mixture may include the (+) and the (−) enantiomer but also the cis and trans-form of a compound. The compounds to be analysed may also be mixtures of diastereomers, for example comprising a first diastereomer as racemic mixture and a second diastereomer as racemic mixture. The molar ratio of the first and second diastereomers may be from 1:1 to 1:100.

The compound to be co-crystallized may further possess planar or helical chirality.

It is further possible that the compound to be co-crystallized comprises up to five, preferable two chemically different compounds, which in turn may consist of a pure enantiomer, but also of a mixture of diastereomers as already described.

In a first variant of the method, the compound to be co-crystallized has a molecular weight of less than 500 g/mol, more preferable less than 250 g/mol.

In a second variant of the method, the compound to be co-crystallized is a liquid (at room temperature/at 20° C.).

In a third variant of the method, the compound and the tetraaryladamantanes according to general formula I are co-crystallized in absence of a solvent. This variant is preferred if the compound is a liquid at room temperature and can act as solvent for the tetraaryladamantanes. In this case, a solution or mixture of the compound and the tetraaryladamantanes may be obtained by heating to for example temperatures between 30 and 170° C.

In any variant, co-crystallization may be induced by heating and subsequent cooling to room temperature or by incubating at room temperature or below room temperature.

If a (additional) solvent is used, care should be taken that the solvent is not built into the co-crystals of the compound and the tetraaryladamantanes. This can be avoided by evaporating the solvent during or even before co-crystallization. The compound to be analysed may also crystallize with the tetraaryladamantane upon standing at room temperature or below room temperature.

In another variant, of the method, the compound and the tetraaryladamantanes are co-crystallized by providing a mixture of the compound, the tetraaryladamantanes and a solvent and subsequent evaporation of the solvent followed by heating or incubation at room temperature.

Preferable, the mixture from which co-crystallization occurs may be obtained by evaporating a solution in a solvent for NMR spectroscopy. This allows the combination of NMR analysis with X-ray diffraction of the compounds. After evaporation of the solvent, either thermally or by directing a gas stream onto the surface, co-crystallization may be induced by heating and subsequent cooling to room temperature or by incubating at room temperature or below.

The X-ray diffraction (X-ray SCD) method used in the method of the invention can be performed as known to the person skilled in the art with the usual software packages like SHELXL97, optionally with absorption correction for example performed with SADBAS.

EXAMPLES

Representative Protocol

A sample of 1,3,5,7-tetrakis(2,4-diethoxyphenyl)adamantane (TEO) (2 mg, 0.0025 mmol) in a glass vial is treated with (R)-(+)-α-methylbenzylamine (30 µL, 29 mg, 0.24 mmol). The resulting suspension is heated on a hot plate with a surface temperature of 150° C. until a homogenous solution forms. The hot plate is switched off, and the solution is allowed to cool to room temperature while on the plate. The crystals formed are harvested and analysed by X-ray diffractometry.

Diffraction data were collected on a KAPPA APEXII DUO diffractometer from Bruker (Karlsruhe, Germany) at 130 K and Cu Kα (λ=1.54178 Å). Cell refinement and data reduction were performed with the SAINT program package. Absorption correction was performed with SADBAS. The structure was solved by direct methods using SHELXL97. An isotropic refinement by least-squares methods were also carried out in SHELXL97. This procedure was followed by anisotropic refinements on F2 of all non-hydrogen atoms. The positions of the H-atoms were calculated geometrically with riding models. The graphics of the crystal structure were generated with the program *Mercury* 4.0.0.

FIG. 1, below, shows the structure of the guest and the host molecule and crystallographic data for either of the two enantiomers of methylbenzylamine.

The entire procedure from the crystallization to the final crystal structure, including the determination of the absolute configuration of the guest, took less than two days.

Figure 2:
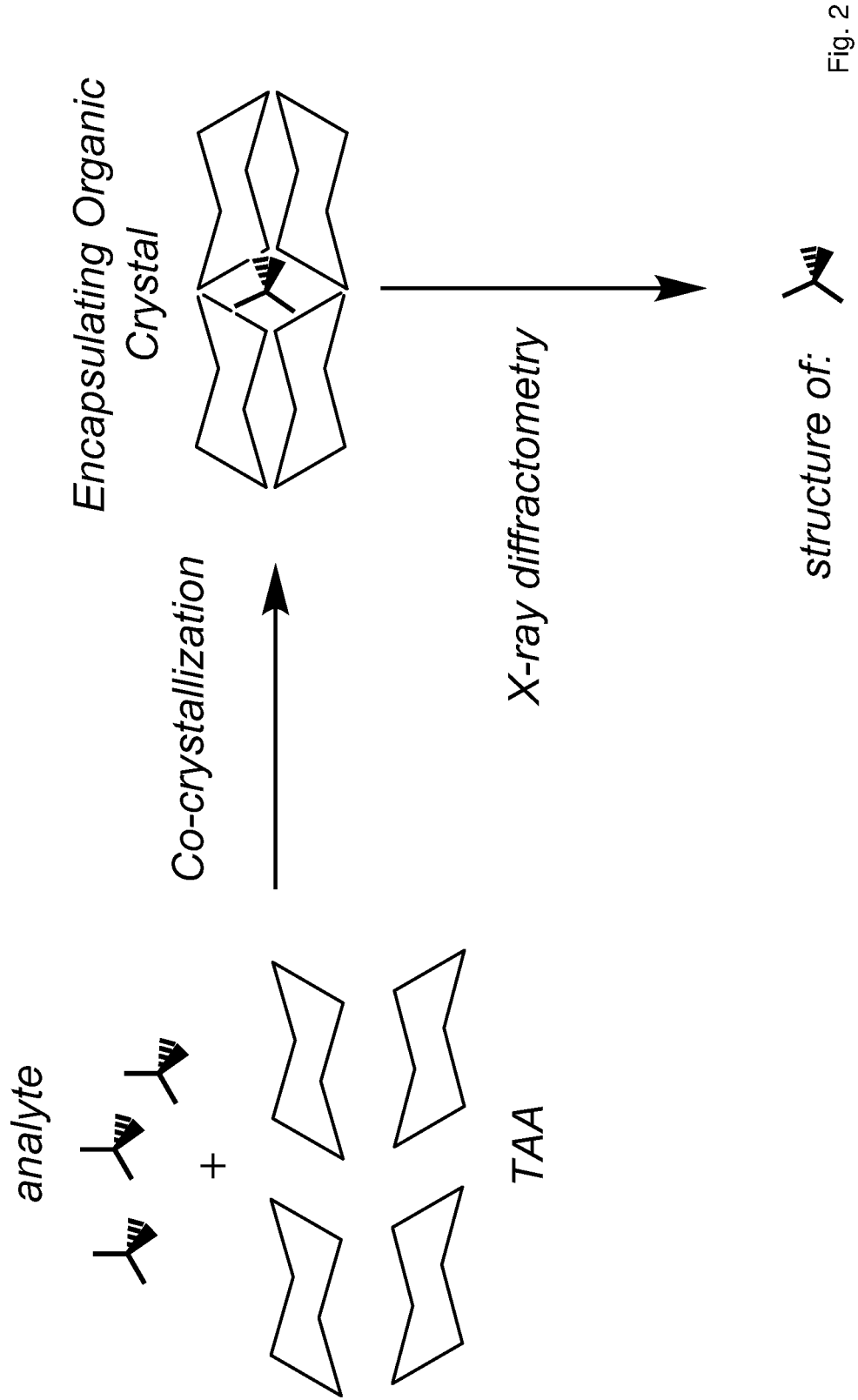
Figure 3A:
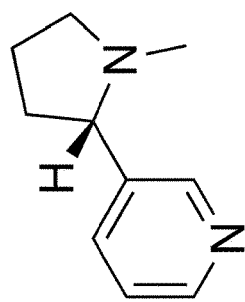
Figure 3A:
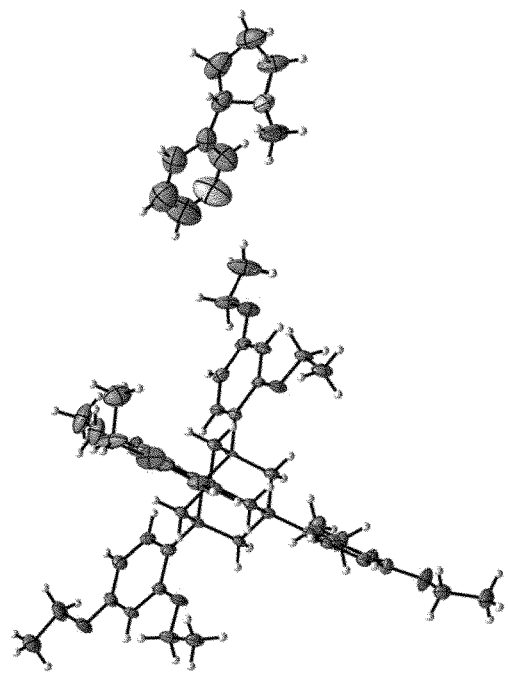
Figure 3A:
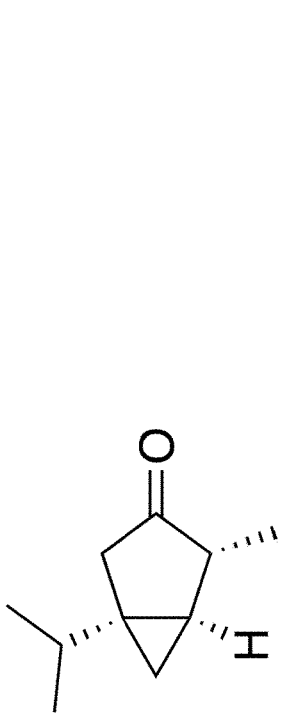
Figure 3A:
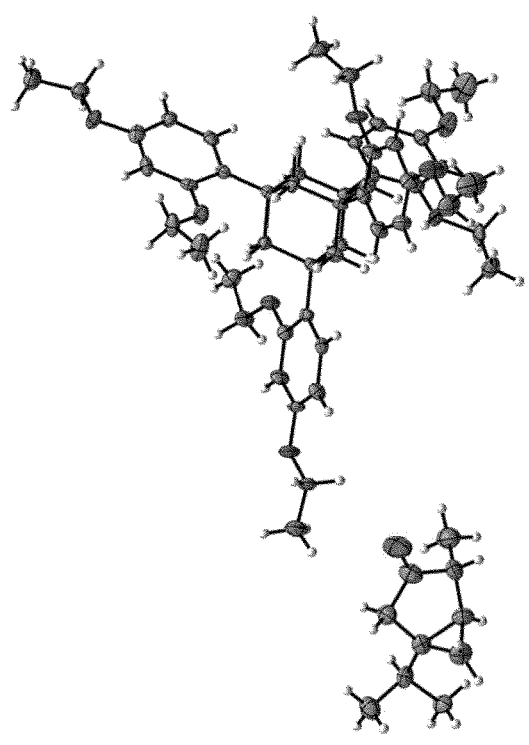
Figure 3B:
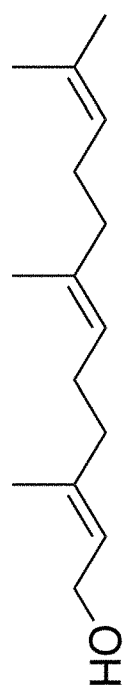
Figure 3B:
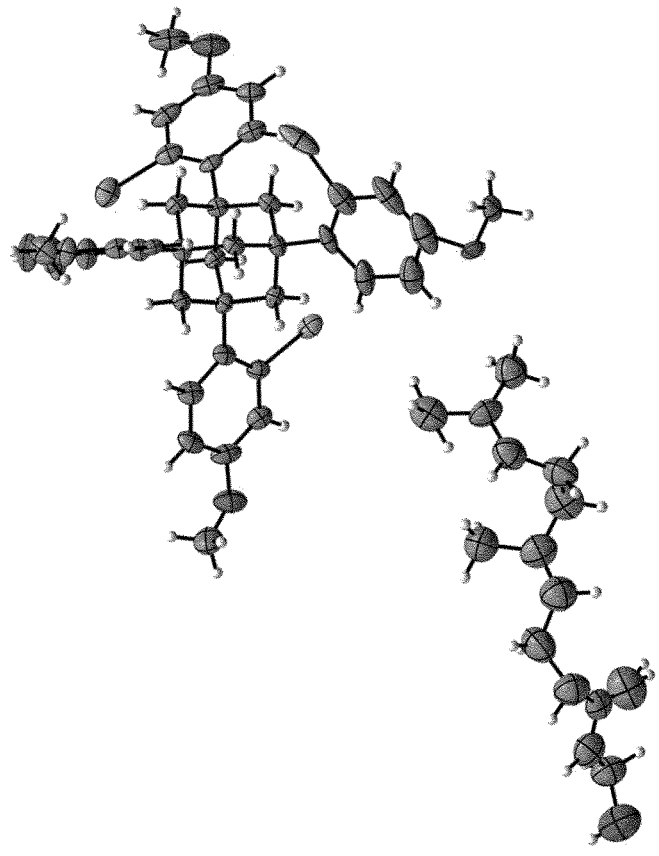
Figure 3B:
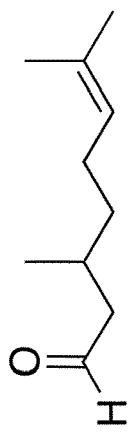
Figure 3B:
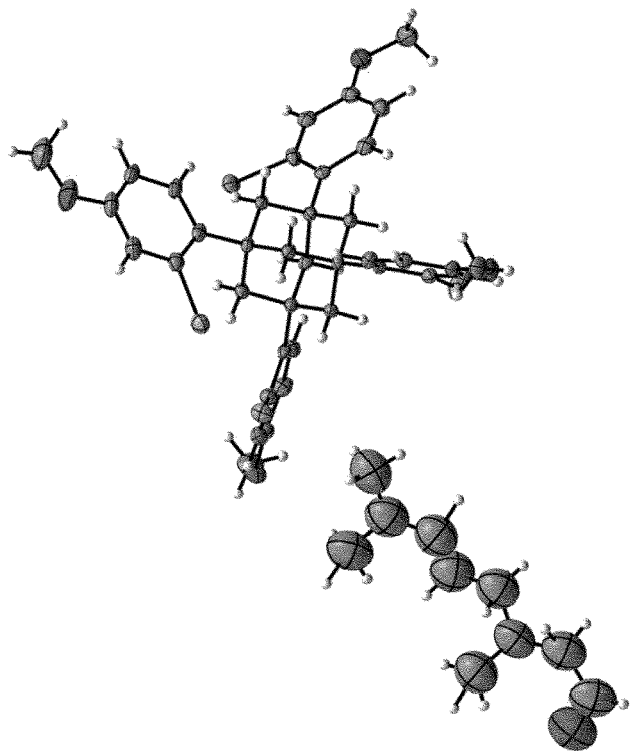
Figure 4:
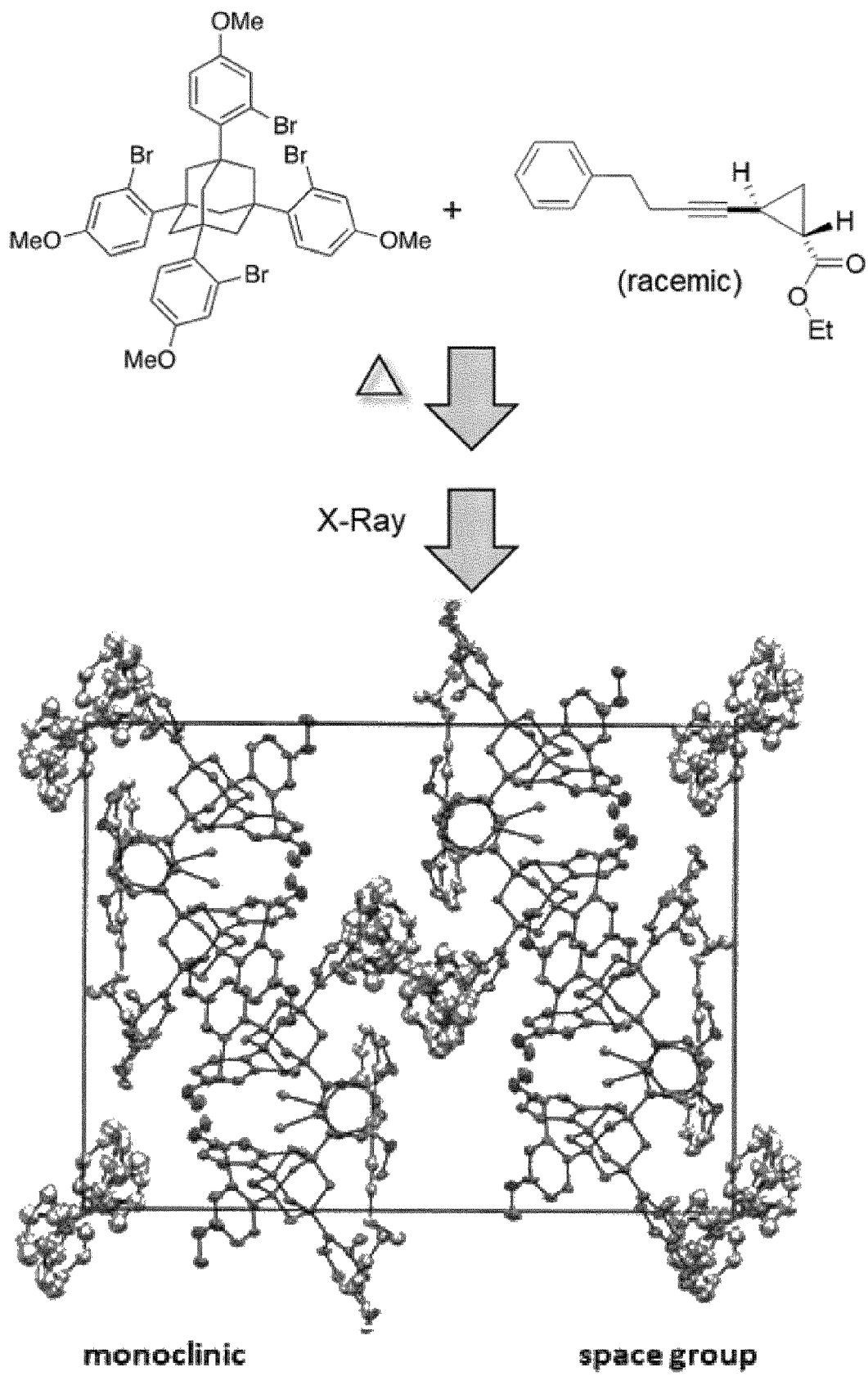

FIG. 2 shows the procedure for structure elucidation. FIGS. 3 and 4 show additional examples for the successful elucidation of the three-dimensional structure of analytes using the procedure.

FIG. 4 shows an example for the successful determination of the relative configuration for a racemic mixture of enantiomers using the method of the invention. The analyte was identified as being of the trans-configuration by co-crystallizing a racemic mixture or a mixture containing racemates of either relative configuration in unequal concentrations (trans as major component and cis as minor component).

The invention claimed is:

1. A method for elucidating the three-dimensional structure of a compounds by X-ray diffraction (X-ray SCD) characterized in that the compound is co-crystallized with tetraaryladamantes according to general formula I

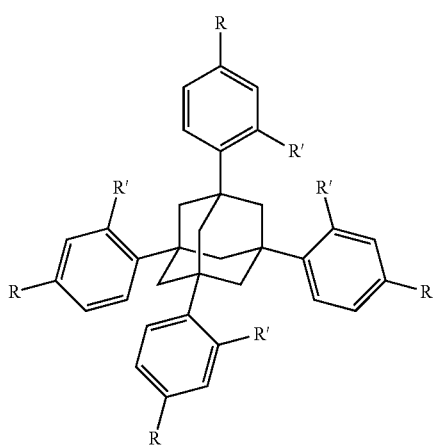

(I)

Wherein R and R' are identical or different residues selected from the group consisting of O—R1, S—R1, NHR1, NR1R2, F, Cl, Br or I and R1, R2 stand for identical or different, substituted on not substituted aliphatic or aromatic residues having 1 to 25 carbon atoms and the three-dimensional structure of the compound is obtained by X-ray diffraction (X-ray SCD) and wherein in the compound is a chiral molecule, and the absolute configuration or relative configuration of the compound is obtained.

2. The method according to claim 1 characterized in that the compound is co-crystallized with tetraaryladamantes into a single-crystal.

3. The method according to claim 1, characterized in that the compound to be co-crystallized has a molecular weight of less than 500 g/mol.

4. The method according to claim 1, characterized in that the compound to be co-crystallized is a liquid.

5. The method according to claim 1, characterized in that the compound and the tetraaryladamantanes are co-crystallized in the absence of a solvent.

6. The method according to claim 1, characterized in that the compound and the tetraaryladamantanes are co-crystallized by providing a mixture of the compound, the tetraaryladamantanes and a solvent and subsequent evaporation of the solvent followed by heating or incubation at room temperature.

7. The method according to claim 1, characterized in that the compound is a mixture of enantiomers or a mixture of diastereomers.

8. A method for elucidating the absolute or relative three dimensional configuration of a chiral compound, comprising:
co crystallizing the compound with tetraaryladamantes according to general formula I

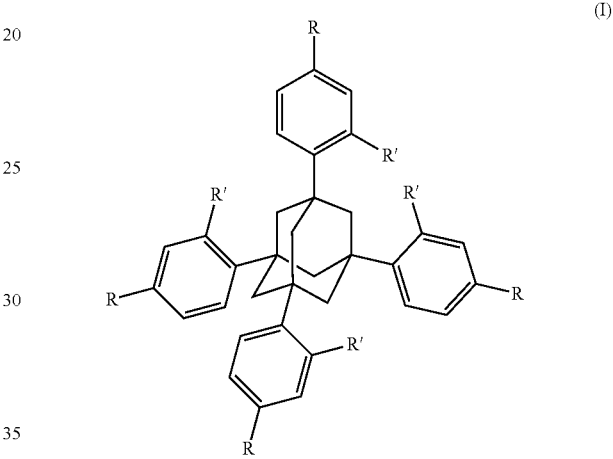

(I)

wherein R and R' are identical or different residues selected from the group consisting of O—R1, S—R1, NHR1, NR1R2, F, Cl, Br or I and R1, R2 stand for
identical or different, substituted on not substituted aliphatic or aromatic residues having 1 to 25 carbon atoms; and
obtaining the absolute or relative three dimensional configuration of the compound by X-ray diffraction (X-ray SCD).

* * * * *